(12) United States Patent
Lin et al.

(10) Patent No.: US 12,364,976 B2
(45) Date of Patent: Jul. 22, 2025

(54) CATALYST SYSTEMS SUITABLE FOR THE TETRAMERIZATION OF ETHYLENE AND METHODS OF USING THE SAME

(71) Applicant: Saudi Arabian Oil Company, Dhahran (SA)

(72) Inventors: Sibo Lin, Arlington, MA (US); Dana Amber Wong, Chestnut Hill, MA (US); Yagnaseni Ghosh, Lexington, MA (US); Motaz Khawaji, Thuwal (SA); Wei Xu, Thuwal (SA); Mohamed Elanany, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 252 days.

(21) Appl. No.: 18/178,808

(22) Filed: Mar. 6, 2023

(65) Prior Publication Data

US 2024/0299921 A1     Sep. 12, 2024

(51) Int. Cl.
| | | |
|---|---|---|
| *B01J 31/00* | (2006.01) | |
| *B01J 31/12* | (2006.01) | |
| *B01J 31/18* | (2006.01) | |
| *C07C 11/02* | (2006.01) | |

(52) U.S. Cl.
CPC .......... *B01J 31/189* (2013.01); *B01J 31/122* (2013.01); *C07C 11/02* (2013.01); *B01J 2231/20* (2013.01); *C07C 2531/14* (2013.01); *C07C 2531/18* (2013.01)

(58) Field of Classification Search
None
See application file for complete search history.

(56) References Cited

U.S. PATENT DOCUMENTS

| | | |
|---|---|---|
| 7,964,763 B2 | 6/2011 | Dixon et al. |
| 8,367,786 B2 | 2/2013 | Dixon et al. |
| 8,461,406 B2 | 6/2013 | Overett et al. |
| 9,035,119 B2 | 5/2015 | Ewart et al. |
| 10,414,698 B2 | 9/2019 | Fern et al. |
| 10,471,416 B2 | 11/2019 | Im et al. |
| 11,440,857 B2 | 9/2022 | Khawaji et al. |
| 11,623,901 B1 | 4/2023 | Jaseer et al. |
| 11,639,321 B1 | 5/2023 | Jaseer et al. |
| 2007/0185357 A1 | 8/2007 | De Boer et al. |
| 2021/0146346 A1 | 5/2021 | Lee et al. |
| 2022/0288573 A1 | 9/2022 | Jaseer et al. |

FOREIGN PATENT DOCUMENTS

| | | |
|---|---|---|
| JP | 2008260723 A | 10/2008 |
| KR | 101471156 B1 | 12/2014 |
| WO | 2004056479 A1 | 7/2004 |
| WO | 2009-046144 A1 | 4/2009 |

OTHER PUBLICATIONS

Notification of Transmittal of the International Search Report and the Written Opinion of the International Searching Authority, or the Declaration dated Apr. 30, 2024 pertaining to International application No. PCT/US2024/013031 filed Jan. 26, 2024, pp. 1-13.
Blann et al., "Ethylene tetramerisation: Subtle effects exhibited by N-substituted diphosphinoamine ligands", Journal of Catalysis, vol. 249, pp. 244-249, 2007.
Bollmann et al., "Ethylene Ttramerization: A New Route to Produce 1-Octene in Exceptionally High Selectives", JACS Communications, vol. 126, pp. 14712-14713, 2004.
Boobier et al., "Machine learning with physicochemical relationships: solubility prediction in organic solvents and water", Nature Communications, vol. 11, No. 5753, 2020, 10 pages.
Do et al., "Spectral Studies of a Cr(PNP)-MAO System for Selective Ethylene Trimerization Catalysis: Searching for the Active Species", American Chemical Society, vol. 3, pp. 2582-2585, 2013.
Kim et al., "MAO-free and extremely active catalytic system for ethylene tetramerization", Applied Organometallic Chemistry, 33:e4829, 2019, 13 pages.
Kuhlmann et al., "N-substituted diphosphinoamines: Toward rational ligand design for the efficient tetramerization of ethylene", Journal of Catalysis, vol. 245, pp. 279-284, 2007.
Lee et al., "Polyhedral oligomeric silsesquioxane-conjugated bis(diphenylphosphino) amine ligand for chromium(III) catalyzed ethylene trimerization and tetramerization", Applied Catalysis A, General, vol. 560-, pp. 21-27, 2018.
Park et al., "Extremely Active Ethylene Tetramerization Catalyst Avoiding the use of Methylaluminoxane: [iPrN{P(C6H4-p-SiR3)2}2CrCl2]+[B(C6F5)4]", ChemCatChem, vol. 11, pp. 1-20, 2019.

*Primary Examiner* — Yun Qian
(74) *Attorney, Agent, or Firm* — DINSMORE & SHOHL LLP

(57) ABSTRACT

Catalyst systems suitable for tetramerizing ethylene to form 1-octene may include a catalyst including a chromium compound coordinated with a ligand and a co-catalyst including an organoaluminum compound. The ligand may have a chemical structure according to Formula (1), wherein $R^1$ is a ($C_3$-$C_{20}$) substituted or unsubstituted hydrocarbyl group; $R^2$, $R^3$, $R^4$, and $R^5$ are independently chosen from ($C_1$-$C_{50}$) hydrocarbyl groups; and $R^1$ and N are in a cis configuration.

20 Claims, No Drawings

CATALYST SYSTEMS SUITABLE FOR THE TETRAMERIZATION OF ETHYLENE AND METHODS OF USING THE SAME

TECHNICAL FIELD

Embodiments of the present disclosure generally relate to chemical processing and, more particularly, to catalyst systems utilized in such chemical processing.

BACKGROUND

Linear alpha-olefins ("LAOs") are typically produced via the cracking of refinery products or the non-selective oligomerization of ethylene, which results in a broad alpha-olefin distribution. Currently, there are several industrial processes that produce LAOs, such as the Shell Higher Olefin Process (SHOP), which has been in operation since 1977. SHOP employs a combination of oligomerization and olefin metathesis chemistries to produce a variety of LAOs using a nickel-based catalyst. INEOS, a global manufacturer of petrochemicals, has also developed a proprietary process for synthesizing a wide range of LAOs with the flexibility to change distributions of products to meet demand.

However, demand for LAOs is rising in North America, Western Europe, and Asia. In particular, demand for short chain alpha olefins, such as 1-octene and 1-hexene, is rising due to their significance to a number of specific applications. For example, 1-octene may be used to improve the rheological melt and solid resin properties of polyethylene. As a result, the main consumer of 1-octene is the industry responsible for the high-volume production of linear low-density polyethylene (LLDPE) and high-density polyethylene (HDPE), which expands each year. The content of 1-octene may be from 1% to 2% in HDPE, and as much as 10% in some LLDPE grades.

Based on this, 1-octene is a significant chemical feedstock that is in market demand. Aside from the processes discussed above, various catalysts have been developed for the tetramerization of ethylene to selectively form 1-octene. However, these catalysts have deficiencies in several respects. Accordingly, improved catalysts, which are suitable for tetramerization of ethylene to selectively form 1-octene, are desired in the industry.

SUMMARY

Fouling, as described in the present disclosure, refers to the undesirable formation of polymers. Such polymers may form as side-products in the reaction of ethylene to form 1-octene when a catalyst system including chromium is used. However, as described in the present disclosure, it has been discovered that a particular ligand that comprises cyclohexane substituted with a diphosphinoamino group (a PNP group) and a hydrocarbyl group on the 1 and 4 carbon atoms of the cyclohexane respectively, where the diphosphinoamino group and the hydrocarbyl group are in a cis configuration, may coordinate with chromium, and may reduce polymeric fouling. As described herein, the cis configuration of the PNP group and the hydrocarbyl group may have beneficial effects for the catalyst system. For example, the use of catalysts including the presently described ligands may improve the solubility of the catalysts in aliphatic solvents, which may result in improved activity of the catalyst system. Moreover, in some embodiments, the utilization of catalysts including the ligands may contribute to maintaining the selectivity of 1-octene, or even enhancing the selectivity of 1-octene, as compared with similar catalyst systems that do not include the ligand.

According to one or more embodiments, a catalyst system suitable for tetramerizing ethylene to form 1-octene may comprise a catalyst comprising a chromium compound coordinated with a ligand; and a co-catalyst comprising an organoaluminum compound, wherein the ligand has the chemical structure according to Formula (1).

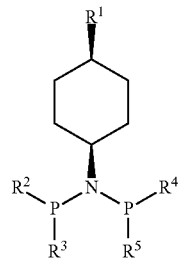

Formula (I)

In Formula (I), $R^1$ is a ($C_3$-$C_{20}$) substituted or unsubstituted hydrocarbyl group; $R^2$, $R^3$, $R^4$, and $R^5$ are independently chosen from ($C_1$-$C_{50}$) hydrocarbyl groups; and $R^1$ and N are in a cis configuration.

Additional features and advantages of the aspects of the present disclosure will be set forth in the detailed description that follows and, in part, will be readily apparent to a person of ordinary skill in the art from the detailed description or recognized by practicing the aspects of the present disclosure.

DETAILED DESCRIPTION

The present disclosure describes catalyst systems that may be utilized to produce 1-octene from ethylene by tetramerization. Also described are methods for utilizing such catalyst systems. The presently described catalyst systems may include a catalyst and a co-catalyst, which are described in detail herein. In one or more embodiments, the catalyst may include chromium and a ligand. The co-catalyst may include an organoaluminum compound. In one or more embodiments, the ligand may include cyclohexane substituted with a diphosphinoamino group and a hydrocarbyl group on the 1 and 4 carbon atoms of the cyclohexane respectively, where the diphosphinoamino group and the hydrocarbyl group are in a cis configuration.

In one or more embodiments, the catalyst systems described in the present disclosure may be used to selectively tetramerize ethylene to produce 1-octene, while reducing undesirable polymerization, sometimes referred to as "fouling" as compared to other known catalysts. Fouling may occur at least partially due to the formation of solid polyethylene-based residues, which may reduce fluid flow and/or fully block or at least partially block fluids in a reactor system from flowing at a desired rate. Without being bound by any particular theory, it is believed that the incorporation of the ligand described in the present disclosure into the catalyst system reduces fouling while maintaining a suitable yield of 1-octene.

It should be understood that the catalyst systems described in the present disclosure may not completely eliminate fouling during a reaction. However, in one or more embodiments, these catalyst systems reduce fouling as compared with catalyst systems that do not include a ligand as described in the present disclosure. Additionally, it should be understood that while these catalyst systems may be useful for the catalysis of the oligomerization of ethylene, such as the tetramerization of ethylene to form 1-octene, they may also be useful for the catalysis of other chemical reactions. As a result, these catalyst systems should not be considered limited in their use to the tetramerization of ethylene to form 1-octene.

Numerous terms and phrases used to describe the embodiments of the present disclosure are now defined and/or described.

As used in the present disclosure, the term "catalyst system" refers to any catalytically functional collection of chemical species. In one or more embodiments, a catalyst system may include a catalyst and a co-catalyst. In some embodiments, a catalyst system may include additional components, such as, for example, additional co-catalysts or non-catalytic additives, which may serve other purposes. Some embodiments described herein are directed to catalyst systems.

As used in the present disclosure, the term "catalyst" refers to any substance that increases the rate of a specific chemical reaction. Catalysts described in this disclosure may be utilized to promote various reactions, such as, but not limited to, the tetramerization of ethylene to form 1-octene. Catalysts are generally not consumed in a reaction, but as would be understood in the art, may have reduced catalytic activity over time and need to be replaced and/or regenerated.

As used in the present disclosure, the term "co-catalyst" (also referred to as an activator and/or scavenger) generally refers to any substance or chemical agent that brings about catalysis of a chemical reaction in conjunction with one or more catalysts. In some embodiments, a catalyst may have independent catalytic functionality, while in other embodiments the catalyst may only have substantial catalytic functionality when paired with a co-catalyst. It should be understood that the catalyst and co-catalyst may be, in some embodiments, bonded or formed in a complex, but in other embodiments are not bonded or present in a complex. Some co-catalysts may be said to "activate" a catalyst, which may increase catalytic functionality.

As used in the present disclosure, the term "independently chosen" means that the R groups, such as, $R^1$, $R^2$, and $R^3$, can be identical or different. For example, $R^1$, $R^2$, and $R^3$ may all be substituted alkyls; or $R^1$ and $R^2$ may be a substituted alkyl, and $R^3$ may be an aryl. A chemical name associated with an R group is intended to convey the chemical structure that is recognized in the art as corresponding to that of the chemical name. As a result, chemical names are intended to supplement and illustrate, not preclude, the structural definitions known to those of skill in the art.

As used in the present disclosure, the term "reaction product" refers to a chemical species formed from the reaction of any two or more reactant species or reagents. A reaction product may result in a covalent or ionic bond, coordination, or other interaction between reactant species. In one or more embodiments, two or more reaction products may result from the reaction of the reactant species, and all of these possible produced chemical species are included in the reaction product.

When used to describe certain carbon atom-containing chemical groups, a parenthetical expression having the form "$(C_x\text{-}C_y)$" means that the unsubstituted form of the chemical group has from x carbon atoms to y carbon atoms, inclusive of x and y. For example, a $(C_1\text{-}C_{50})$ alkyl group is an alkyl group having from 1 to 50 carbon atoms in its unsubstituted form. In some embodiments and general structures, certain chemical groups may be substituted by one or more substituents. A substituted chemical group defined using the "$(C_x\text{-}C_y)$" parenthetical may contain more than y carbon atoms depending on the identity of any substituents. For example, a "$(C_1\text{-}C_{50})$ alkyl substituted with exactly one phenyl ($—C_6H_5$)" may contain from 7 to 56 carbon atoms. Thus, in general when a chemical group defined using the "$(C_x\text{-}C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom (—H) bonded to a carbon atom or heteroatom of a corresponding unsubstituted compound or functional group is replaced by a substituent. Substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "—H" means a hydrogen or hydrogen radical that is covalently bonded to another atom. "Hydrogen" and "—H" are interchangeable, and unless clearly specified have identical meanings.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus.

The term "cyclohydrocarbyl" means an aromatic or non-aromatic, cyclic hydrocarbyl having at least three carbon atoms, including monocyclic and polycyclic hydrocarbyls, fused and non-fused polycyclic hydrocarbyls, and bicyclic hydrocarbyls, non-aromatic saturated or unsaturated cyclic hydrocarbyls, and substituted or unsubstituted hydrocarbyls.

The term "aryl" means an aromatic hydrocarbon radical, in which the carbon atoms of the aromatic system may be substituted or unsubstituted. Aryls include monocyclic, bicyclic and tricyclic aromatic hydrocarbon radicals. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Non-limiting examples of aryls include phenyl; fluorenyl; tetrahydrofluorenyl; indacenyl; hexahydroindacenyl; indenyl; dihydroindenyl; naphthyl; tetrahydronaphthyl; and phenanthrenyl.

The term "alkyl" means a saturated hydrocarbon radical that may be linear or branched. Accordingly, the term "$(C_1\text{-}C_{20})$ alkyl" means a saturated linear or branched hydrocarbon radical of from 1 to 20 carbon atoms that is unsubstituted or substituted. Examples of unsubstituted ($C_1$-$C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

As noted previously herein, the embodiments of the present disclosure are directed to a catalyst system suitable for tetramerizing ethylene to form 1-octene. In one or more embodiments, the catalyst system includes a catalyst. In some embodiments, the catalyst includes chromium. It should be understood that, as contemplated in the present disclosure, a catalyst that includes chromium may be any chemical compound that includes a chromium atom and is catalytically functional for a reaction such as, without limitation, promoting the tetramerization of ethylene to from 1-octene.

In one or more embodiments, the catalyst includes a chromium compound and a ligand. It should be understood that the chromium complexes described herein, which may coordinate with one or more ligands, are not necessarily limited in structure, but include chromium. In some embodiments, the chromium compound includes an organic chromium salt, an inorganic chromium salt, a chromium coordination, a chromium organometallic complex, or combinations of these. In one or more embodiments, the chromium compounds may be chromium (II) compounds or chromium (III) compounds comprising carboxylates, acetylacetonates, halides or combinations of these. In some embodiments, the chromium compound chosen from one or more of a chromium trichloride tris-tetrahydrofuran complex. (benzene)tricarbonyl chromium, chromium (III) octanoate, chromium (III) acetylacetonate, chromium hexacarbonyl, chromium (III) 2-ethylhexanoate, [$CrCl_2$($\mu$-Cl)(THF)$_2$]$_2$, $CrCl_2$(THF)$_2$, Chromium(III) pyridine-2-carboxylate, and Tris(2,2,6,6-tetramethyl-3,5-heptanedionato)chromium(III).

The chromium compound may be produced using procedures and methods known in the art. For example, procedures and methods for producing chromium compounds are described in U.S. Pat. No. 7,297,832, which is incorporated by reference herein in its entirety.

It should be understood that the ligands described herein, which may coordinate with the chromium atom of the chromium compound are not necessarily limited in structure, unless specified. In one or more embodiments, the ligand may comprise cyclohexane substituted with a diphosphinoamino group (a PNP group) and a hydrocarbyl group on the 1 and 4 carbon atoms of the cyclohexane ring respectively, where the diphosphinoamino group and the hydrocarbyl group are in a cis configuration. In one or more embodiments, the ligand may have a structure according to Formula (I):

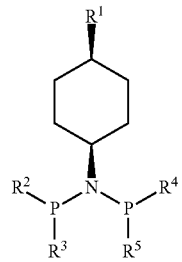

Formula (I)

In Formula (I), $R^1$ is a ($C_3$-$C_{20}$) substituted or unsubstituted hydrocarbyl group. In one or more embodiments, $R^1$ may be cyclic, polycyclic, or acyclic. In one or more embodiments, $R^1$ may be linear or branched. In one or more embodiments, $R^1$ is a ($C_3$-$C_{20}$) substituted hydrocarbyl group comprising one or more heteroatoms. In such embodiments, the one or more heteroatoms may comprise one or more of boron, nitrogen, oxygen, fluorine, phosphorous, silicon, sulfur, and chlorine. For example, $R^1$ may comprise a thioether group or an alkoxy group.

In one or more embodiments, $R^1$ may be a ($C_3$-$C_{20}$) unsubstituted hydrocarbyl group. The unsubstituted hydrocarbyl group may be cyclic, acyclic, or polycyclic. In one or more embodiments, the unsubstituted hydrocarbyl group may be linear or branched. In one or more embodiments, $R^1$ may be a ($C_3$-$C_{20}$) alkyl group. The alkyl group may be linear or branched. In one or more embodiments, $R^1$ may be n-butyl, isopropyl, octadecyl, n-dodecyl, or n-tetradecyl.

As shown in Formula (I), $R^1$ and N are in a cis configuration on the cyclohexane ring. As described herein, a "cis configuration" refers to a configuration in which the substituents are on the same side of a moiety. For example, in the chemical structure illustrated in Formula (I), both $R^1$ and the N of the PNP group are positioned on the same side of the cyclohexane ring. Specifically, $R^1$ and the N of the PNP group are positioned so that they are protruding out of the page in the same direction from the cyclohexane ring. Accordingly, $R^1$ and N are in a cis configuration in Formula (I). Without intending to be bound by theory, when $R^1$ and N are in a cis configuration, the cyclohexane has two near-degenerate chair conformations, each with an axial substituent. This may hinder molecular stacking of the ligand, which in turn may improve the solubility of the ligand in aliphatic solvents. The use of aliphatic solvents in the catalyst system may result in increased catalyst activity and reduced polymer formation during ethylene tetramerization reactions.

Still referring to Formula (I), $R^2$, $R^3$, $R^4$, and $R^5$ may be independently chosen from ($C_1$-$C_{50}$) hydrocarbyl groups. In embodiments, the ($C_1$-$C_{50}$) hydrocarbyl group may be a substituted or unsubstituted ($C_1$-$C_{50}$) linear or branched hydrocarbyl group, a substituted or unsubstituted ($C_3$-$C_{50}$) cyclohydrocarbyl group, or a substituted or unsubstituted ($C_4$-$C_{50}$) aryl group. In some embodiments the ($C_1$-$C_{50}$) hydrocarbyl group may be a ($C_1$-$C_{50}$) heterohydrocarbyl group, a ($C_3$-$C_{50}$) heterocyclohydrocarbyl group, or a ($C_4$-$C_{50}$) heteroaryl group. In one or more embodiments, $R^2$, $R^3$, $R^4$, and $R^5$ may be independently chosen from ($C_4$-$C_{50}$) aryl groups.

In some embodiments, $R^2$, $R^3$, $R^4$, and $R^5$ of Formula (I) may be independently chosen from a benzyl, phenyl, tolyl, xylyl, mesityl, biphenyl, naphthyl, anthracenyl, methoxy, ethoxy, and other alkoxy, phenoxy, tolyloxy, and other aryloxy, dimethylamino, diethylamino, methylethylamino, thiophenyl, pyridyl, thioethyl, thiophenoxy, trimethylsilyl, dimethylhydrazyl, methyl, ethyl, and other alkyl, ethenyl, propenyl, and other alkenyl, propyl, butyl, and other alkyl, propynyl, and other alkynyl, cyclopentyl, cyclohexyl, and other cycloalkyl, ferrocenyl, or tetrahydrofuranyl group. In one or more embodiments, each of $R^2$, $R^3$, $R^4$, and $R^5$ are phenyl groups.

In some embodiments, $R^2$ and $R^3$ or $R^4$ and $R^5$ may be bonded such that a cyclic moiety including P is formed. For example, $R^2$ and $R^3$ may be bonded such that a cyclic moiety including P is formed. Likewise, $R^4$ and $R^5$ may be bonded such that a cyclic moiety including P is formed. In one or more embodiments, $R^2$, $R^3$, and P may form a phospholane group. In one or more embodiments, $R^4$, $R^5$, and P may form a phospholane group. As described herein, a "phospholane group" refers to a cyclic organophosphorous compound comprising a five membered ring including phosphorous and four carbon atoms. In some embodiments, the phospholane compound may be unsubstituted or may be substituted by one or more hydrocarbyl groups. Cyclic moieties that may be formed from $R^2$, $R^3$, and P or $R^4$, $R^5$, and P in some embodiments are depicted in Formulas (II) to (IX).

Formula (II)

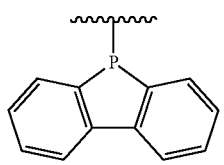

Formula (III)

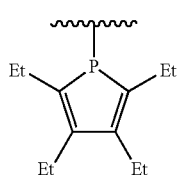

Formula (IV)

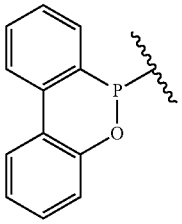

Formula (V)

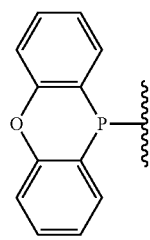

Formula (VI)

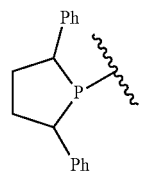

Formula (VII)

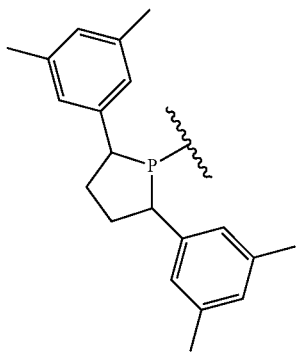

Formula (VIII)

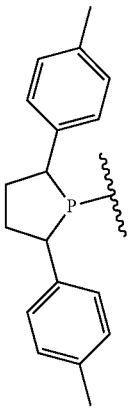

Formula (IX)

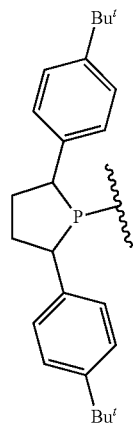

In one or more embodiments, the ligand is chosen from cis-1-bis(diphenylphosphino)amino-4-butylcyclohexane, or cis-1-bis(diphenylphosphino)amino-4-isopropylcyclohexane, or cis-1-bis(diphenylphosphino)amino-4-dodecylcyclohexane.

In one or more embodiments, the catalyst may include the ligand in an amount such that a molar ratio of the ligand to the chromium compound in the catalyst system is from 1.0 to 2.0. For example, the molar ratio of the ligand to chromium in the catalyst system may be from 1.0 to 2.0, from 1.1 to 2.0, from 1.2 to 2.0, from 1.3 to 2.0, from 1.4 to 2.0, from 1.5 to 2.0, from 1.6 to 2.0, from 1.7 to 2.0, from 1.8 to 2.0, from 1.9 to 2.0, from 1.0 to 1.9, from 1.0 to 1.8, from 1.0 to 1.7, from 1.0 to 1.6, from 1.0 to 1.5, from 1.0 to 1.4, from 1.0 to 1.3, from 1.0 to 1.2, from 1.0 to 1.1, or any combination of ranges formed from these endpoints. In one or more embodiments, the molar ratio of the ligand to the chromium compound in the catalyst system is from 1.0 to 1.2. Without intending to be bound by theory, if the molar ratio of the ligand to chromium is greater than 2.0, the activity of the catalyst system may be reduced.

In one or more embodiments, the catalyst system also includes a co-catalyst. In some embodiments, the co-catalyst may include an organoaluminum compound. As described in the present disclosure, the term "organoaluminum compound" refers to any chemical compound that includes at least one aluminum atom and any organic moiety. It should be appreciated that the organoaluminum compound may include several chemical species, or may be a single chemical species. In some embodiments, the organoaluminum compound may be an alkyl aluminum compound. The aluminum alkyl compound may, for example, have a structure according to Formula (X):

Formula (X)

In Formula (X), $R^6$, $R^7$, and $R^8$ are each independently chosen from hydrogen, an unsubstituted ($C_1$-$C_{20}$) linear or branched alkyl group, an oxygen-containing moiety, or a halide. In some embodiments, the alkyl aluminum compound may be an aluminoxane structure (a partial hydrolysate of a trialkylaluminum compound). For example, suitable aluminum alkyl compounds may include trimethylaluminium, triethylaluminum, tripropylaluminum, tri-iso-butylaluminum, diisobutylaluminium hydride, tri-hexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), isobutylaluminoxane (iBAO), and modified alkylaluminoxanes, such as modified methylaluminoxane (MMAO). As described in the present disclosure, the term "modified alkylaluminoxane" refers to an alkylaluminoxane that includes one or more modifier groups, such as isobutyl or n-octyl groups in addition to the alkyl groups. In one or more embodiments, the organoaluminum compound of the catalyst system may comprise, consist essentially of, or consist of any of these compounds.

In one or more embodiments, the catalyst system may include the co-catalyst in an amount such that a molar ratio of the organoaluminum compound to the chromium compound in the catalyst system is from 100 to 5000. For example, the molar ratio of aluminum to chromium in the catalyst system may be from 100 to 5000, from 300 to 5000, from 500 to 5000, from 700 to 5000, from 900 to 5000, from 1100 to 5000, from 1300 to 5000, from 1500 to 5000, from 1700 to 5000, from 1900 to 5000, from 2100 to 5000, from 2300 to 5000, from 2500 to 5000, from 2700 to 5000, from 2900 to 5000, from 3100 to 5000, from 3300 to 5000, from 3500 to 5000, from 3700 to 5000, from 3900 to 5000, from 4100 to 5000, from 4300 to 5000, from 4500 to 5000, from 4700 to 5000, from 4900 to 5000, from 100 to 4800, from 100 to 4600, from 100 to 4400, from 100 to 4200, from 100 to 4000, from 100 to 3800, from 100 to 3600, from 100 to 3400, from 100 to 3200, from 100 to 3000, from 100 to 2800, from 100 to 2600, from 100 to 2400, from 100 to 2200, from 100 to 2000, from 100 to 1800, from 100 to 1600, from 100 to 1400, from 100 to 1200, from 100 to 1000, from 100 to 800, from 100 to 600, from 100 to 400, from 100 to 300, or any combination of ranges formed from these endpoints. In one or more embodiments, the molar ratio of aluminum to chromium in the catalyst system may be from 300 to 1000. Without intending to be bound by theory, when the ratio of organoaluminum compound to the chromium compound is less than 100, the catalyst activity may be reduced. When the ratio is less than 100, trace impurities may react with chromium instead of being scavenged by aluminum. Furthermore, when the ratio of organoaluminum compound to the chromium compound is greater than 5000, the formation of polymer byproducts may increase.

The catalyst system may further comprise one or more solvents. In one or more embodiments, the catalyst system comprises an aliphatic solvent. As described herein, an "aliphatic solvent" refers to an unsaturated hydrocarbon solvent. Generally, aliphatic solvents do not include aromatic rings. In one or more embodiments, the aliphatic solvent may comprise alkanes, cycloalkanes, unsaturated derivatives of alkanes and cycloalkanes, or combinations of these. For example, the aliphatic solvent may comprise hexane, heptane, cyclohexane (CyH), methylcyclohexane (MeCy), and 2,2,4-trimethylpentane (TMP). Without intending to be bound by theory, the use of an aliphatic solvent in the catalyst system may result in increased catalyst activity and reduced polymer formation during ethylene tetramerization reactions as compared to other solvents.

In embodiments, the catalyst system may further comprise halogenated solvents. For example, the catalyst system may comprise chlorobenzene, fluorobenzene, dichloromethane, 1,1-dichloroethane, 1,2-dichloroethane, and ortho-, meta-, and para-isomers of dihalobenzenes. Without intending to be bound by theory, halogenated solvents may be used to improve the solubility of the chromium compound.

In one or more embodiments, the catalyst system may be free from halogenated solvents. In one or more embodiments, the catalyst system may be free from aromatic solvents. Furthermore, in one or more embodiments, the catalyst system may be free from both aromatic and halogenated solvents. Without intending to be bound by theory, the use of aromatic and halogenated solvents may lower 1-octene selectivity, lower catalyst activity, and increase the rate of polymer formation in ethylene tetramerization reactions. Without intending to be bound by theory, aromatic solvents may form $Cr(arene)_2$ sandwich complexes with the chromium compound, which may reduce the activity of the catalyst system. Furthermore, the use of halogenated and aromatic solvents in the catalyst system may increase the cost and complexity of solvent recycling systems. In some embodiments, it may be beneficial to increase the amount of aliphatic solvent and reduce the amount of aromatic and halogenated solvents in the catalyst system. In some embodiments, the solvent may consist of one or more aliphatic solvents.

In one or more embodiments, ethylene may be contacted with the catalyst system to from a reaction product including 1-octene. Contacting may generally include any mixing and/or combining of the reactant ethylene with the catalyst system. In some embodiments, the catalyst and co-catalyst may be separately prepared as solutions, and then combined, prior to contacting of the catalyst system with ethylene. In some embodiments, the catalyst system may be contacted with ethylene in the presence of one or more reaction mediums. Suitable reaction mediums may include aliphatic solvents. For example, suitable reaction mediums may comprise cyclohexane (CyH), methylcyclohexane (MeCy), chlorobenzene (PhCl), and 2,2,4-trimethylpentane (TMP). In some embodiments, the ethylene may be contacted with the catalyst system in the presence of hydrogen.

In one or more embodiments, the reaction may be performed as a batch reaction or as a continuous process reaction, such as a continuous stir tank reactor process. In some embodiments, the reaction may be performed at a pressure from 2 bar to 100 bar (such as from 10 bar to 50 bar). For example, the reaction may occur at a pressure from 2 bar to 100 bar, from 10 bar to 100 bar, from 20 bar to 100 bar, from 30 bar to 100 bar, from 40 bar to 100 bar, from 50 bar to 100 bar, from 60 bar to 100 bar, from 70 bar to 100 bar, from 80 bar to 100 bar, from 90 bar to 100 bar, from 2 bar to 90 bar, from 2 bar to 80 bar, from 2 bar to 70 bar, from 2 bar to 60 bar, from 2 bar to 50 bar, from 2 bar to 50 bar, from 2 bar to 40 bar, from 2 bar to 30 bar, from 2 bar to 20 bar, from 2 bar to 10 bar, or any combination of ranges formed from these endpoints. In one or more embodiments, the reaction may be performed at a temperature from 30° C. to 120° C. (such as from 30° C. to 75° C.). For example, the reaction may be performed at a temperature from 30° C. to 120° C., from 40° C. to 120° C., from 50° C. to 120° C., from 60° C. to 120° C., from 70° C. to 120° C., from 80° C. to 120° C., from 90° C. to 120° C., from 100° C. to 120° C., from 110° C. to 120° C. from 30° C. to 110° C., from 30° C. to 100° C., from 30° C. to 90° C., from 30° C. to 80° C., from 30° C. to 70° C. from 30° C. to 60° C., from 30° C. to 50° C., from 30° C. to 40° C., or any combination of ranges formed from these endpoints. However, process conditions outside of these ranges are contemplated, especially in view of the specific design of the reactor system and concentrations of the reactants and catalyst system.

It should be understood that, in one or more embodiments, similar catalyst systems that do not include the ligand of the present application may exhibit increased fouling compared to the catalyst system of the present application. In one or more embodiments, the inclusion of the ligand in a catalyst system may suppress polymer formation while not greatly reducing the yield of 1-octene. In one or more embodiments, polymer formation (fouling) may be reduced by at least 5%, 10%, 20%, 30%, 40%, 50%, 60%, 70%, 80%, 90%, or even 95% by the inclusion of the ligand. For example, the reaction product of the tetramerization of ethylene using the catalyst system may include less than 15 wt. %, less than 12 wt. %, less than 9 wt. %, less than 6 wt. %, or less than 3 wt. % of polymer.

In one or more embodiments. 1-octene production may be increased, stay the same, or may decrease by less than or equal to 50%, 40%, 30%, 20%, 10% or even 5% by the inclusion of the ligand. For example, the reaction product of the tetramerization of ethylene using the catalyst system may include greater than 50 wt. %, greater than 55 wt. %, greater than 60 wt. %, greater than 65 wt. %, or greater than 70 wt. % of 1-octene.

In one or more embodiments, the catalyst system may both reduce the polymer formation (such as by at least 5%, 10%, 20%, 30%, 40%, 50%, 60%, 70%, 80%, 90% or even 95%) and increase, not effect, or decrease 1-octene production rate by less than or equal to 50%. 40%, 30%, 20%, 10% or even 5%. Reduction in polymer formation rates and catalytic activity on a percentage basis are based on catalyst systems that include the ligand of the present disclosure as compared with catalyst systems that do not include the ligand of the present disclosure.

In one or more embodiments, the catalyst system may have increased activity compared to similar catalyst systems that do not include the ligand of the present disclosure. As used in the present disclosure, the term "activity" refers to the amount of reaction product produced (in kilograms) per the amount of chromium compound used (in grams) per hour ($kg \cdot g_{Cr}^{-1} \cdot h^{-1}$). In some embodiments, the catalyst system may have an activity greater than $10\ kg \cdot g_{Cr}^{-1} \cdot h^{-1}$, greater than $100\ kg \cdot g_{Cr}^{-1} \cdot h^{-1}$, greater than $250\ kg \cdot g_{Cr}^{-1} \cdot h^{-1}$, greater than $500\ kg \cdot g_{Cr}^{-1} \cdot h^{-1}$, or greater than $750\ kg \cdot g_{Cr}^{-1} \cdot h^{-1}$.

EXAMPLES

The various aspects of the present disclosure will be further clarified by the following examples. The examples are illustrative in nature and should not be understood to limit the subject matter of the present disclosure.

Example 1—Preparation of a Ligand

A ligand was formed as depicted in Reaction Scheme 1:

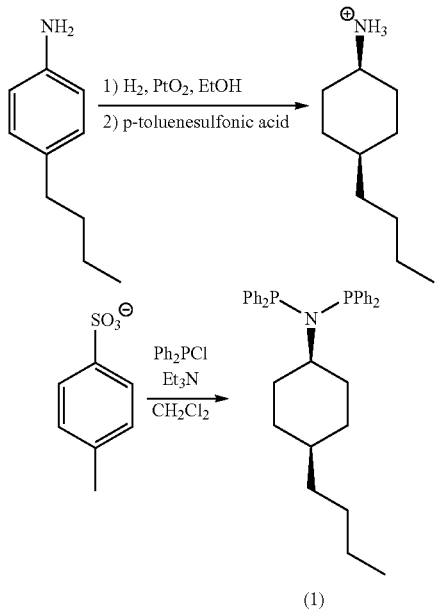

The glass liner of a reaction vessel was loaded with 1.2 mL (7.6 mmol) of 4-n-butylaniline, 0.73 mL (12.8 mmol) of acetic acid, and 116 mg (0.51 mmol) of $PtO_2$. The glass liner was inserted into a Biotage Endeavor parallel pressurized reactor and sealed by securing the reactor head. Hydrogenation proceeded under the following steps and conditions that were performed using the Endeavor Advanced Software. The impeller stirring rate was set to 500 RPM. The reactor was pressurized with nitrogen to about 4 bar for about 10 seconds then was vented to a pressure of about 1 bar. This nitrogen purge sequence was repeated ten times. Then, the reactor was pressurized with hydrogen gas to about 30 bar and was then vented to a pressure of about 1 bar. This hydrogen purge sequence was repeated four times. Hydrogen was added to the reactor as needed to maintain a pressure of 480 psi for 24 hours. The reactor was then vented, and its contents were filtered through Celite with the aid of 30 mL of ethanol. The filtrate was concentrated on a vacuum rotary evaporator. The resulting residue was treated with 15 mL of diethyl ether, 30 mL of water and 1.28 g (32 mmol) of NaOH and was transferred to a separation funnel.

The organic layer was isolated, and the aqueous layer was further extracted with 3 cycles of 15 mL of diethyl ether. The combined organic phases were dried with $MgSO_4$, filtered, and concentrated to an oil including the hydrogenated 4-n-butylaniline (0.36 g).

A 20 mL scintillation vial was loaded with the hydrogenated 4-n-butylaniline (0.36 g, 2.32 mmol), p-toluenesulfonic acid monohydrate (0.436 g, 2.29 mmol), tetrahydrofuran (5 mL), and a magnetic stir bar. The vial was sealed and placed in an aluminum heating block that was preheated to 70° C. The vial was heated for 1 hour. Then, the vial was transferred to a refrigerator. After chilling overnight, crystals of cis-1-ammonium-4-n-butylcyclohexane tosylate were isolated by filtration. The isolation yielded 0.43 g (1.31 mmol) of product.

In an inert atmosphere glovebox, a 20 mL scintillation vial was loaded with the cis-1-ammonium-4-n-butylcyclohexane tosylate (1.26 g, 3.85 mmol), 3 mL of dichloromethane, 2.68 mL of trimethylamine (19.24 mmol), and a magnetic stir bar. The mixture was stirred and 1.715 g of diphenylphosphinochloride (7.77 mmol) was added to the mixture dropwise. The vial was capped and stirring continued at room temperature. After two hours, the mixture formed a gel and stirring was stopped. 2 mL of dichloromethane were added to the mixture and stirring resumed. The reaction continued for 3 days. Volatiles were removed from the vial under vacuum. Then, the reaction mixture was suspended in diethylether and filtered to remove triethylammonium chloride. The filtrate was concentrated under vacuum until white solids began to precipitate out of solution. Two volumetric equivalents of acetonitrile were added to further induce precipitation. The white precipitate was collected by filtration and rinsed with MeCN. The filtrate was dried under vacuum to obtain 1.114 g of cis-1-bis(diphenylphosphino) amino-4-n-butylcyclohexane, Product (1) shown in Reaction Scheme 1.

In addition to cis-1-bis(diphenylphosphino)amino-4-n-butylcyclohexane, two other ditopic ligands were formed using methods analogous to the method described in the present example. These two ligands are cis-1-bis(diphenylphosphino)amino-4-iso-propylcyclohexane and cis-1-bis(diphenylphosphino)amino-4-n-dodecylcyclohexane.

Example 2—Ethylene Tetramerization

Several ethylene tetramerization reactions were performed using the following general procedure to compare the cis-1-bis(diphenylphosphino)amino-4-n-butylcyclohexane ligand of Example 1 to a comparative ligand (N-isopropyl-bis(diphenylphosphino)amine). A 300 mL Hastelloy reactor equipped with an overhead stirrer and an internal thermocouple was weighed, heated to 160° C., and then subjected to 100 cycles of alternating evacuation and pressurization with 5 bar nitrogen before cooling to the desired reaction temperature. Meanwhile, reactor chargers A and B were purged overnight. Reactor chargers are stainless steel chambers each containing an inlet and an outlet quarter-turn valve. Reactor charger A was loaded with 44.8 g of process solvent and then 154.2 mg of MMAO-3A solution (7 wt. % Al in heptane, purchased from Nouryon; 400 µmol Al). Reactor charger B was loaded with a Cr precursor ($CrCl_3$ $(THF)_3$) as 2 wt. % stock solution in precatalyst solvent (0.8 µmol Cr); the ligand (0.864 µmol) as 0.2 wt. % stock solution in the ligand solvent); and process solvent to bring the overall contents of reactor charger B to 3.85 g. The process solvent, ligand solvent, and precatalyst solvents were varied between different ethylene tetramerization runs, as shown in Tables 1 and 2 below.

Reactor charger A and B were each attached to the reactor under a counterflow of nitrogen. The charger-reactor transfer lines were purged with alternating cycles of evacuation and pressurization with an inert gas. Reactor charger A was pressurized with 3 bar of inert gas and then opened to the reactor. The contents of Reactor charger A were transferred to the reactor by a combination of pressure and gravity. The stirrer speed was set to 300 RMP and the reactor was brought to a temperature of 45° C. Reactor charger B was pressured with 6 bar of inert gas and the contents of Reactor charger B were transferred to the reactor. The stirrer speed was increased to 1500 RPM and the reactor was pressurized with ethylene to a pressure of 53 bar (45 bar of ethylene). Ethylene was supplied to the reactor as necessary to keep the reactor pressure constant during the reaction.

After the desired reaction time of 60 minutes, ethylene was no longer fed to the reactor and the stirrer was slowed to 300 RPM. The reactor was immersed in an ice water bath. When the temperature of the reactor reached about 10° C., the reactor pressure was released and MeOH was added to quench the reaction. After 15 minutes, the reactor was removed from the ice water bath and the stirrer was stopped. The reactor was weighed to determine the net weight gain. A sample of the liquid products was mixed with a calibrated amount of nonane and analyzed by gas chromatography to determine the yield of liquid products. The product mixture was separated by centrifugation at 3000 RPM for 5 minutes to separate the polymer products from the liquid products.

Reactions were performed by the method described above using the cis-1-bis(diphenylphosphino)amino-4-n-butylcyclohexane ligand of Example 1 (Ligand 1) and a comparative ligand (N-isopropyl-bis(diphenylphosphino)amine) (Ligand 2). Reactions were performed using various process solvents, ligand solvents, and precatalyst solvents. The process solvents tested were PhCl, MeCy and PhF. The ligand solvents tested were PhCl and MeCy, and the precatalyst solvents tested were PhCl and PhF. The various reaction results are summarized in Tables 1 and 2 below.

TABLE 1

Ethylene Tetramerization comparing
Ligand 1 to Comparative Ligand 2

| Ligand | Process Solvent | Activity (kg/gCr/h) | 1-Octene (wt. %) | 1-Hexene (wt. %) | Polyethylene (wt. %) |
|---|---|---|---|---|---|
| 1 | PhCl | 478.3 | 63.8 | 18.9 | 2.1 |
| 2 | PhCl | 368.0 | 68.3 | 17.6 | 1.6 |
| 1 | MeCy | 655.0 | 66.3 | 10.2 | 1.9 |
| 2 | MeCy | 261.9 | 71.5 | 10.7 | 1.3 |

The results in Table 1 indicate that the cis-1-bis(diphenylphosphino)amino-4-n-butylcyclohexane ligand of Example 1 (Ligand 1) outperforms the comparative ligand (Ligand 2), particularly in the aliphatic (MeCy) process solvent.

TABLE 2

Performance of Ligand 1 in Various Solvents

| Ligand | Precursor Solvent | Ligand Solvent | Process Solvent | Activity (kg/gCr/h) | 1-Octene (wt. %) | 1-Hexene (wt. %) | Polyethylene (wt. %) |
|---|---|---|---|---|---|---|---|
| 1 | PhCl | PhCl | PhCl | 715.4 | 60.4 | 22.9 | 1.0 |
| 1 | PhCl | PhCl | MeCy | 655.0 | 66.3 | 10.2 | 1.9 |
| 1 | PhF | MeCy | MeCy | 796.0 | 65.3 | 8.9 | 1.5 |
| 1 | PhF | MeCy | MeCy | 584.1 | 67.4 | 10.0 | 1.8 |
| 1 | PhF | MeCy | PhF | 441.0 | 70.6 | 10.7 | 1.4 |

The results in Table 2 show that the cis-1-bis(diphenylphosphino)amino-4-n-butylcyclohexane ligand of Example 1 (Ligand 1) retains similar activity in a variety of solvents. However, the use of chlorobenzene may result in a reduced yield of 1-octene.

Further ethylene tetramerization reactions were performed to compare the cis-1-bis(diphenylphosphino)amino-4-n-butylcyclohexane ligand of Example 1 (Ligand 1), the cis-1-bis(diphenylphosphino)amino-4-iso-propylcyclohexane ligand (Ligand 3), the cis-1-bis(diphenylphosphino)amino-4-n-dodecylcyclohexane ligand (Ligand 4), and a comparative ligand (Comparative Ligand 5) having the chemical structure according to Formula (XI).

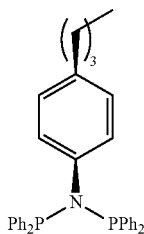

Formula (XI)

Each of the four ligands were used in an ethylene tetramerization reaction under the following conditions. The chromium compound was 1 µmol of $Cr(TMHD)_3$. The molar ratio of ligand to the chromium compound was 1. The organoaluminum compound was 2 mmol of MMAO-3A. The molar ratio of organoaluminum compound to chromium compound was 2000. The solvent was heptane and the total solution volume was 100 mL. The ethylene tetramerization reaction was performed at a pressure of 45 bar and a temperature of 60° C. for a time of 10 minutes. The products and catalyst activity for each reaction are listed in Table 3.

TABLE 3

| Ligand | 1 | 3 | 4 | 5 |
|---|---|---|---|---|
| $C_6$ (wt. %) | 20 | 20.2 | 22.6 | 26.8 |
| 1-Hexene in $C_6$ (%) | 79.5 | 77 | 81.1 | 76.4 |
| 1-Hexene (wt. %) | 15.9 | 15.6 | 18.3 | 20.6 |
| $C_6$ cyclics (wt. %) | 4.1 | 4.6 | 4.3 | 6.3 |
| $C_8$ (wt. %) | 78.4 | 78.9 | 76.5 | 71.5 |
| 1-Octene in $C_8$ (%) | 94.4 | 94.9 | 94.3 | 85.1 |
| 1-Octene (wt. %) | 74 | 74.9 | 72.1 | 60.9 |
| $C_{10}$ (wt. %) | 0.4 | 0.8 | 0.8 | 1.6 |
| 1-Hexene + 1-Octene (wt. %) | 89.9 | 90.4 | 90.5 | 81.5 |
| Polyethylene (wt. %) | 1.2 | >0.1 | >0.1 | >0.1 |
| Activity (Kg/gCr/h) | 655 | 643 | 443 | 197 |

Each of the four ligand were used in another ethylene tetramerization reaction under the following conditions. The chromium compound was 1 µmol of $Cr(TMHD)_3$. The molar ratio of ligand to the chromium compound was 1. The organoaluminum compound was 2 mmol of MMAO-3A. The molar ratio of organoaluminum compound to chromium compound was 2000. The solvent was heptane and the total solution volume was 100 mL. The ethylene tetramerization reaction was performed at a pressure of 45 bar and a temperature of 45° C. for a time of 10 minutes. The products and catalyst activity for each reaction are listed in Table 4.

TABLE 4

| Ligand | 1 | 3 | 4 | 5 |
|---|---|---|---|---|
| $C_6$ (wt. %) | 17.3 | 20.4 | 16.8 | 35 |
| 1-Hexene in $C_6$ (%) | 70.1 | 77.1 | 69.4 | 98.3 |
| 1-Hexene (wt. %) | 12.1 | 15.7 | 11.7 | 34.4 |
| $C_6$ cyclics (wt. %) | 5.2 | 4.7 | 5.1 | 0.7 |
| $C_8$ (wt. %) | 80.4 | 79.4 | 82 | 63.9 |
| 1-Octene in $C_8$ (%) | 93.4 | 88.5 | 96.4 | 64.5 |
| 1-Octene (wt. %) | 75.1 | 70.3 | 79 | 41.2 |
| $C_{10}$ (wt. %) | 0.7 | 0.1 | 1.1 | 0 |
| 1-Hexene + 1-Octene (wt. %) | 87.2 | 86 | 90.7 | 75.6 |
| Polyethylene (wt. %) | 1.6 | >0.1 | >0.1 | >0.1 |
| Activity (Kg/gCr/h) | 502 | 288 | 718 | 84 |

Example 3—Solubility of Ligands in Aliphatic Solvents

The solubility of the cis-1-bis(diphenylphosphino)amino-4-n-butylcyclohexane ligand of Example 1 was analyzed as described below. $^{31}P\{^1H\}$ NMR spectra were recorded with long relaxation delay (d1=30 seconds) over 64 scans (ns=64) with a coaxial insert (Wilmad-Lab Glass #WGS-5BL) loaded with a solution of triphenylphosphine in tetrahydrofuran as an integration standard. The relative integral of a saturated solution of the cis-1-bis(diphenylphosphino)amino-4-n-butylcyclohexane ligand of Example 1 in methylcyclohexane was 6.53, while the relative integral of a saturated solution of benchmark ligand N-isopropyl-bis(diphenylphosphino)amine in methylcyclohexane is only 5.82. This indicates that the molar solubility of the cis-1-bis(diphenylphosphino)amino-4-n-butylcyclohexane ligand of Example 1 is 12% greater than the benchmark ligand in methylcyclohexane.

In a first aspect of the present disclosure, a catalyst system suitable for tetramerizing ethylene to form 1-octene comprises a catalyst comprising a chromium compound coordinated with a ligand; and a co-catalyst comprising an organoaluminum compound, wherein the ligand has the chemical structure according to Formula (1), where $R^1$ is a $(C_3-C_{20})$ substituted or unsubstituted hydrocarbyl group; $R^2$, $R^3$, $R^4$, and $R^5$ are independently chosen from $(C_1-C_{50})$ hydrocarbyl groups; and $R^1$ and N are in a cis configuration.

A second aspect of the present disclosure may include the first aspect, wherein $R^1$ is a $(C_3-C_{20})$ unsubstituted hydrocarbyl group.

A third aspect of the present disclosure may include the first or second aspects, wherein $R^1$ is a $(C_3-C_{20})$ alkyl group.

A fourth aspect of the present disclosure may include the first aspect, wherein $R^1$ is a $(C_3-C_{20})$ substituted hydrocarbyl group comprising one or more heteroatoms.

A fifth aspect of the present disclosure may include the fourth aspect, wherein the one or more heteroatoms are chosen from boron, nitrogen, oxygen, fluorine, phosphorous, silicon, sulfur, chlorine, and combinations thereof.

A sixth aspect of the present disclosure may include any of the first through fifth aspects, wherein $R^2$, $R^3$, $R^4$, and $R^5$ are independently chosen from $(C_1-C_{50})$ cyclohydrocarbyl groups.

A seventh aspect of the present disclosure may include any of the first through sixth aspects, wherein $R^2$, $R^3$, $R^4$, and $R^5$ are independently chosen from $(C_4-C_{50})$ aryl groups.

An eighth aspect of the present disclosure may include any of the first through seventh aspects, wherein each of $R^2$, $R^3$, $R^4$, and $R^5$ are phenyl groups.

A ninth aspect of the present disclosure may include any of the first through eighth aspects, wherein the ligand is chosen from cis-1-bis(diphenylphosphino)amino-4-butylcyclohexane, or cis-1-bis(diphenylphosphino)amino-4-isopropylcyclohexane, or cis-1-bis(diphenylphosphino)amino-4-dodecylcyclohexane.

A tenth aspect of the present disclosure may include any of the first through ninth aspects, wherein the catalyst system further comprises an aliphatic solvent.

An eleventh aspect of the present disclosure may include the tenth aspect, wherein the aliphatic solvent comprises one or more of alkanes and cycloalkanes.

A twelfth aspect of the present disclosure may include any of the first through eleventh aspects, wherein the chromium compound comprises one or more of an organic chromium salt, an inorganic chromium salt, a chromium coordination, and a chromium organometallic complex.

A thirteenth aspect of the present disclosure may include any of the first through twelfth aspects, wherein the chromium compound is chosen from one or more of chromium trichloride tris-tetrahydrofuran complex, (benzene)tricarbonyl chromium, chromium (III) octanoate, chromium (III) acetylacetonate, chromium hexacarbonyl, and chromium (III) 2-ethylhexanoate.

A fourteenth aspect of the present disclosure may include any of the first through thirteenth aspects, wherein a molar ratio of the ligand to the chromium compound is from 1.0 to 2.0.

A fifteenth aspect of the present disclosure may include any of the first through fourteenth aspects, wherein the organoaluminum compound has a structure according to Formula (X), wherein $R^6$, $R^7$, and $R^8$ are each selected from the group consisting of a hydrogen atom and an unsubstituted $(C_1-C_{20})$ linear or branched alkyl group.

A sixteenth aspect of the present disclosure may include any of the first through fifteenth aspects, wherein the organoaluminum compound is chosen from one or more of trimethylaluminium, triethylaluminum, tripropylaluminum, tri-iso-butylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

A seventeenth aspect of the present disclosure may include any of the first through sixteenth aspects, wherein a molar ratio of the organoaluminum compound to the chromium compound is from 100 to 5000.

In an eighteenth aspect of the present disclosure, a method for tetramerizing ethylene to form 1-octene comprises contacting ethylene with a catalyst system to form a product comprising 1-octene, wherein the catalyst system comprises: a catalyst comprising a chromium compound coordinated with a ligand; and a co-catalyst comprising an organoaluminum compound, wherein the ligand has the chemical structure according to Formula (1), where $R^1$ is a $(C_3-C_{20})$ substituted or unsubstituted hydrocarbyl group; $R^2$, $R^3$, $R^4$, and $R^5$ are independently chosen from $(C_1-C_{50})$ hydrocarbyl groups; and $R^1$ and N are in a cis configuration.

A nineteenth aspect of the present disclosure may include the eighteenth aspect, wherein the 1-octene is formed at a pressure of from 5 bar to 120 bar.

A twentieth aspect of the present disclosure may include the eighteenth or nineteenth aspects, wherein the 1-octene is formed at a temperature of from 20° C. to 130° C.

The subject matter of the present disclosure has been described in detail and by reference to specific embodiments. It should be understood that any detailed description of a feature of an embodiment does not necessarily imply that the feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It should be understood that any two quantitative values assigned to a property may constitute a range of that property, and all combinations of ranges formed from all stated quantitative values of a given property are contemplated in this disclosure.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." It should be understood that where a first component is described as "comprising" a second component, it is contemplated that, in some embodiments, the first component "consists" or "consists essentially of" that second component. The transitional phrase "consisting of" excludes any element, step, or ingredient not specified in the claim, and the transitional phrase "consisting essentially of" is a limitation to the specified materials or steps and those that do not materially affect the basic and novel characteristics of the claimed embodiment.

The invention claimed is:

1. A catalyst system suitable for tetramerizing ethylene to form 1-octene, the catalyst system comprising:
   a catalyst comprising a chromium compound coordinated with a ligand; and
   a co-catalyst comprising an organoaluminum compound, wherein:
the ligand has the chemical structure:

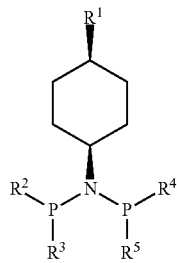

$R^1$ is a ($C_3$-$C_{20}$) substituted or unsubstituted hydrocarbyl group;
$R^2$, $R^3$, $R^4$, and $R^5$ are independently chosen from ($C_1$-$C_{50}$) hydrocarbyl groups; and
$R^1$ and N are in a cis configuration.

2. The catalyst system of claim 1, wherein $R^1$ is a ($C_3$-$C_{20}$) unsubstituted hydrocarbyl group.

3. The catalyst system of claim 1, wherein $R^1$ is a ($C_3$-$C_{20}$) alkyl group.

4. The catalyst system of claim 1, wherein $R^1$ is a ($C_3$-$C_{20}$) substituted hydrocarbyl group comprising one or more heteroatoms.

5. The catalyst system of claim 4, wherein the one or more heteroatoms are chosen from boron, nitrogen, oxygen, fluorine, phosphorous, silicon, sulfur, chlorine, and combinations thereof.

6. The catalyst system of claim 1, wherein $R^2$, $R^3$, $R^4$, and $R^5$ are independently chosen from ($C_1$-$C_{50}$) cyclohydrocarbyl groups.

7. The catalyst system of claim 1, wherein $R^2$, $R^3$, $R^4$, and $R^5$ are independently chosen from ($C_4$-$C_{50}$) aryl groups.

8. The catalyst system of claim 1, wherein each of $R^2$, $R^3$, $R^4$, and $R^5$ are phenyl groups.

9. The catalyst system of claim 1, wherein the ligand is chosen from cis-1-bis(diphenylphosphino)amino-4-butylcyclohexane, or cis-1-bis(diphenylphosphino)amino-4-isopropylcyclohexane, or cis-1-bis(diphenylphosphino)amino-4-dodecylcyclohexane.

10. The catalyst system of claim 1, wherein the catalyst system further comprises an aliphatic solvent.

11. The catalyst system of claim 10, wherein the aliphatic solvent comprises one or more of alkanes and cycloalkanes.

12. The catalyst system of claim 1, wherein the chromium compound comprises one or more of an organic chromium salt, an inorganic chromium salt, a chromium coordination, and a chromium organometallic complex.

13. The catalyst system of claim 1, wherein the chromium compound is chosen from one or more of chromium trichloride tris-tetrahydrofuran complex, (benzene)tricarbonyl chromium, chromium (III) octanoate, chromium (III) acetylacetonoate, chromium hexacarbonyl, tris(2,2,6,6-tetramethyl-3,5-heptanedionato) chromium (III), and chromium (III) 2-ethylhexanoate.

14. The catalyst system of claim 1, wherein a molar ratio of the ligand to the chromium compound is from 1.0 to 2.0.

15. The catalyst system of claim 1, wherein the organoaluminum compound has a structure:

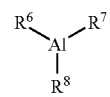

wherein $R^6$, $R^7$, and $R^8$ are each selected from the group consisting of a hydrogen atom and an unsubstituted ($C_1$-$C_{20}$) linear or branched alkyl group.

16. The catalyst system of claim 1, wherein the organoaluminum compound is chosen from one or more of trimethylaluminium, triethylaluminum, tripropylaluminum, tri-iso-butylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

17. The catalyst system of claim 1, wherein a molar ratio of the organoaluminum compound to the chromium compound is from 100 to 5000.

18. A method for tetramerizing ethylene to form 1-octene, the method comprising contacting ethylene with a catalyst system to form a product comprising 1-octene, wherein the catalyst system is the catalyst system of claim 1.

19. The method of claim 18, wherein the 1-octene is formed at a pressure of from 5 bar to 120 bar.

20. The method of claim 18, wherein the 1-octene is formed at a temperature of from 20° C. to 130° C.

* * * * *